US007743765B2

(12) United States Patent
Hodson et al.

(10) Patent No.: US 7,743,765 B2
(45) Date of Patent: *Jun. 29, 2010

(54) INHALATION DEVICE

(75) Inventors: Darren Hodson, Shropshire (GB); Jorgen Rasmussen, Struer (DK)

(73) Assignee: Astrazeneca AB, Sodertalje (SE)

(*) Notice: Subject to any disclaimer, the term of this patent is extended or adjusted under 35 U.S.C. 154(b) by 1183 days.

This patent is subject to a terminal disclaimer.

(21) Appl. No.: 11/346,557

(22) Filed: Feb. 3, 2006

(65) Prior Publication Data
US 2006/0213504 A1 Sep. 28, 2006

Related U.S. Application Data

(63) Continuation-in-part of application No. 10/698,950, filed on Nov. 3, 2003, now Pat. No. 7,367,333, which is a continuation of application No. 09/986,941, filed on Nov. 13, 2001, now abandoned, which is a continuation of application No. 09/214,757, filed as application No. PCT/SE98/02038 on Nov. 11, 1998, now abandoned.

(30) Foreign Application Priority Data
Nov. 14, 1997 (SE) .................................... 9704185

(51) Int. Cl.
*A61M 11/00* (2006.01)
(52) U.S. Cl. .............................. 128/200.23; 128/200.14
(58) Field of Classification Search ............ 128/200.14, 128/200.16, 200.21, 200.23, 200.24, 200.12, 128/203.12, 203.14, 203.15, 203.19, 203.21–203.23; 222/153.01–153.04, 153.1–153.14, 182
See application file for complete search history.

(56) References Cited

U.S. PATENT DOCUMENTS

| 3,456,644 A | 7/1969 | Theil | 128/200.23 |
| 3,506,004 A | 4/1970 | Mann et al. | 128/200.23 |
| 3,521,643 A | 7/1970 | Toth | 128/202.21 |
| 3,636,949 A | 1/1972 | Kropp | 128/200.23 |

(Continued)

FOREIGN PATENT DOCUMENTS

WO 95/07723 3/1995

(Continued)

*Primary Examiner*—Justine R Yu
*Assistant Examiner*—Kristen C Matter
(74) *Attorney, Agent, or Firm*—Finnegan, Henderson, Farabow, Garrett & Dunner, LLP

(57) ABSTRACT

Actuator for an inhaler for delivering medicament by inhalation, having a main body with a tubular member for receiving a canister containing medicament and having a valve stem extending therefrom; and an outlet assembly, as a part formed separately of the main body, including a mouthpiece for guiding medicament to the mouth of a user and a nozzle block for receiving the valve stem of the canister and delivering medicament from the canister into the mouthpiece. The actuator belongs to a range of inhaler actuators where the outlet assembly is a common part for the range of actuators, and the members of the range of actuators differ by the physical appearance of the main body. The outlet assembly is formed such that it has all parts of the actuator that come into contact with the medicament during normal use, and the main body and the outlet assembly are configured so as to snap-fit together and are provided with complementary snap catch members.

37 Claims, 5 Drawing Sheets

U.S. PATENT DOCUMENTS

| | | | |
|---|---|---|---|
| 3,739,950 A | 6/1973 | Gorman | |
| 3,789,843 A | 2/1974 | Armstrong et al. | 128/200.23 |
| 3,818,908 A | 6/1974 | Phillips | 128/200.14 |
| 4,534,343 A | 8/1985 | Nowacki et al. | 128/200.23 |
| 4,576,157 A * | 3/1986 | Raghuprasad | 128/200.23 |
| 4,641,644 A | 2/1987 | Andersson et al. | |
| 4,796,614 A | 1/1989 | Nowacki et al. | 128/200.14 |
| 4,834,083 A | 5/1989 | Byram et al. | 128/200.23 |
| 5,027,808 A | 7/1991 | Rich et al. | 128/203.23 |
| 5,060,643 A | 10/1991 | Rich et al. | 128/200.23 |
| 5,184,761 A | 2/1993 | Lee | 222/402.2 |
| 5,217,004 A | 6/1993 | Blasnik et al. | 128/200.23 |
| 5,460,171 A * | 10/1995 | Pesenti et al. | 128/200.23 |
| 5,482,030 A * | 1/1996 | Klein | 128/200.23 |
| 5,520,166 A | 5/1996 | Ritson et al. | |
| 5,564,414 A * | 10/1996 | Walker et al. | 128/200.23 |
| 5,809,997 A * | 9/1998 | Wolf | 128/200.23 |
| 5,823,394 A | 10/1998 | Davis et al. | 222/137 |
| 5,855,307 A * | 1/1999 | Biddick et al. | 224/267 |
| 5,904,139 A * | 5/1999 | Hauser | 128/200.23 |
| 6,220,243 B1 * | 4/2001 | Schaeffer et al. | 128/203.15 |
| 6,277,749 B1 | 8/2001 | Funabashi | |
| 6,427,684 B2 | 8/2002 | Ritsche et al. | 128/200.23 |
| 6,494,201 B1 | 12/2002 | Welik | 128/200.23 |
| 6,805,116 B2 * | 10/2004 | Hodson et al. | 128/200.23 |
| 7,367,333 B2 * | 5/2008 | Hodson et al. | 128/200.23 |

FOREIGN PATENT DOCUMENTS

| | | |
|---|---|---|
| WO | 96/04948 | 2/1996 |
| WO | 96/04949 | 2/1996 |

\* cited by examiner

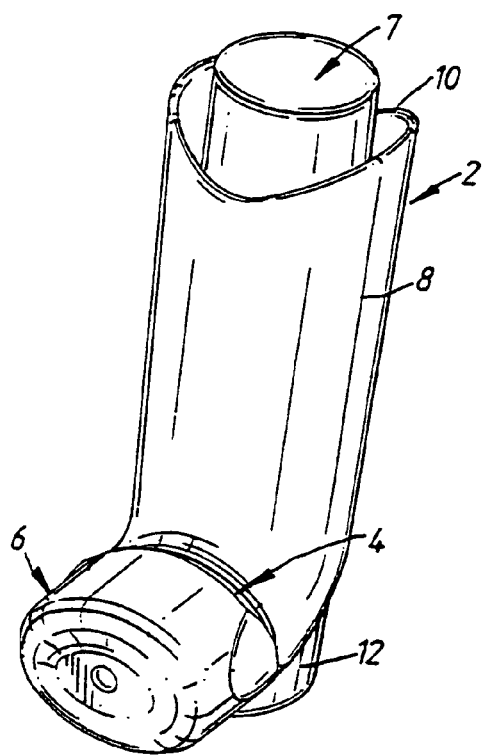
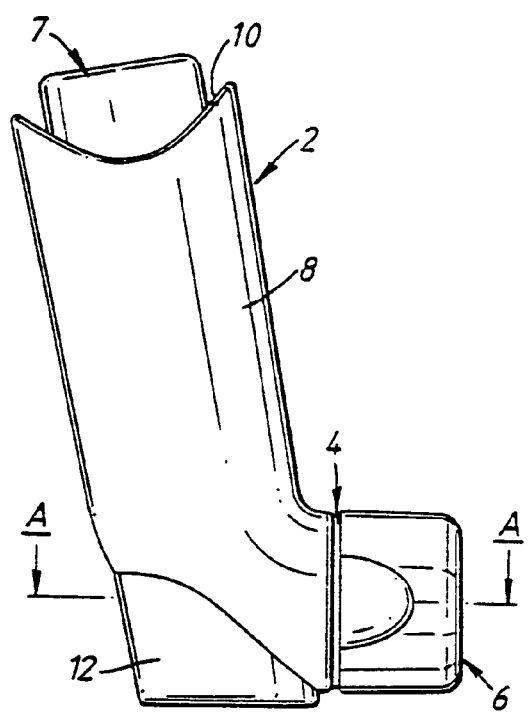
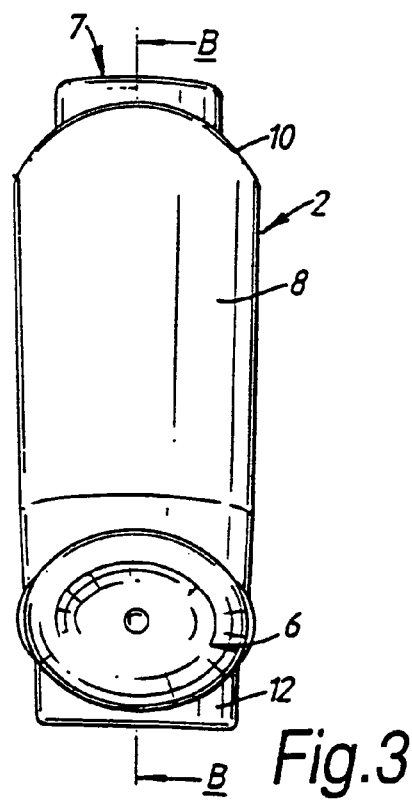
Fig.1
Fig.2
Fig.3

INHALATION DEVICE

This application is a continuation-in-part of application Ser. No. 10/698,950, filed Nov. 3, 2003, now U.S. Pat. No. 7,367,333, which is a continuation of application Ser. No. 09/986,941, filed Nov. 13, 2001, abandoned, which is a continuation of 09/214,757, filed Jan. 12, 1999, abandoned, which is a 371 of PCT/SE98/02038, filed Nov. 11, 1998, the entire content of which is hereby incorporated by reference in this application.

The present invention relates to an actuator for an inhaler for administering medicament by inhalation and to an inhaler including the same.

BACKGROUND OF THE INVENTION

For some time, actuators have been known for delivering metered doses of medicament from aerosol canisters. Conventionally, these actuators comprise a single integral moulding in plastic material. After use with only one canister the actuator is discarded. This is desirable, since some medicaments which are delivered, will, over time, become deposited in the nozzle block and the mouthpiece of the actuator. One problem with such integral moulding actuators, is related to the fact that they often have to be provided in a number of different colours to indicate the medicament being delivered. In order to secure that the colour indication cannot be removed or fade away, a range of differently coloured actuators are conventionally moulded by using plastic material of different colour. However, even though all actuators are made of the same plastic material, they differ in composition as they all include different dyes or pigments. Due to this, each actuator in the range must undergo extensive evaluation in the regulatory phase.

U.S. Pat. No. 5,520,166 discloses a cassette for use in an aerosol delivery device. The cassette comprises, as separate parts, a mouthpiece and an elongated housing to one end of which the mouthpiece is attached. The cassette is intended to be located within a separate actuation device, whereby its external physical appearance is effectively determined by the cassette receiving section of the actuation device. The mouthpiece is attached as a lid at one end of the housing.

SUMMARY OF THE INVENTION

It is an aim of the present invention to provide an actuator of two-part construction, with an outlet assembly comprising those components which come into contact with medicament and a main body comprising the remainder. In this way, it is possible to allow for the manufacture of a range of actuators by providing the outlet assembly as a common part to the range and forming the main body from a material having different constitution and optionally any shape. Typically, the main body can be coloured or have a particular surface finish or decoration according to the medicament to be delivered. In addition, the second part can be formed to have a particular shape, such as that of an animal which may appeal to young children. Such two part construction is also advantageous for preparing regulatory documentation for each member of the range of actuators, as the documentation basically will be the identical for all members in the range including data relating to the common outlet assembly.

The outlet assembly can be provided as a replaceable part, whereby the main body is reused with several canisters, but the outlet assembly is replaced when changing the canister. In this way the amount of waste is reduced, and in order to reduce the amount further, the material volume of the outlet assembly should be minimised. Moreover, an actuator with a replaceable outlet assembly makes it possible for patients to keep a "personalized" actuator for a longer period of time without risk for deteriorated performance due to medications deposited in the nozzle block etc without the need for extensive cleaning, simply by replacing the outlet assembly when switching canister. According to one embodiment, the outlet assembly is arranged to deform or optionally break when removed from the main body, whereby it must be replaced In order to maximise the freedom of design of the main body, it is desired that the outlet assembly, which most likely is of another colour than the main body, constitutes as small part of the actuator external surface as possible.

Accordingly, the present invention provides an actuator for an inhaler for delivering medicament by inhalation, comprising: a main body comprising a tubular member for receiving a canister containing medicament and having a valve stem extending therefrom; and an outlet assembly, as a part formed separately of the main body, comprising a mouthpiece for guiding medicament to the mouth of a user and a nozzle block for receiving the valve stem of the canister and delivering medicament from the canister into the mouthpiece; wherein the actuator belongs to a range of inhaler actuators, the outlet assembly is a common part for the range of actuators and the members of the range of actuators differs by the physical appearance of the main body.

The provision of a range of actuator bodies all being arranged to be fitted with a common outlet assembly, not only simplifies the regulatory process, it also makes the production of a large range of actuators less expensive, as each mould does not include the nozzle block etc. whereby the moulds can be made less complex. Moreover it makes it possible to provide actuators with a functional or even appealing appearance.

According to one embodiment, members of the range of actuators differ in that their respective main bodies are made of materials having different constitution.

According to one embodiment, members of the range of actuators differ by the colour of their respective main bodies, e.g. to distinguish inhalers containing different medicaments and/or doses.

According to one embodiment, members of the range of actuators differ by the surface finish of their respective main bodies, e.g. to make it possible to distinguish inhalers non visually.

According to one embodiment, members of the range of actuators differ by the decoration of their respective main bodies.

According to one embodiment, members of the range of actuators differ by the shape of their respective main bodies. According to one embodiment, the main body is given a particular shape that appeals to a specific patient group. The main body can be shaped to resemble an object other than an actuator for an inhaler, e.g. an animal, a cartoon figure, a plant, a fruit, a toy, a car, or an electronic device, etc. Moreover, the actuator may comprise a protection cap to be placed over the mouthpiece of the outlet assembly, said cap being an integrated part of the particular shape in the protecting position.

The concept of providing main bodies of different physical appearance gives completely new possibilities regarding the selection of inhalers that can be provided. The actuator can be given a physical appearance that is appealing in a manner that certain persons, e.g. children, find it more joyful to take their medication in that the actuator is coloured or shaped as an animal or the like, or e.g. teenagers, find it better acceptance for bringing their inhaler in that it is stylish etc. Members in a family where more than one person takes medicaments by use of an inhaler may select personalized actuators. Moreover, a patient may choose to acquire a highly personalized actuator main body, which might be kept and reused for a long period of time. One type of personalized main body may comprise attachment means for a key strap, a belt strap or a wrist strap to enable it to be carried around the neck, waist or wrist of the patient. Hence, the actuator according the present invention might for some patients make it more joyful to take their prescribed doses, and thus improves their medical treatment. For other patients, the personalized appearance of the actuator might improve the possibilities that they always remember or choose to bring the inhaler, thus again improving their medical treatment.

According to one embodiment, the main body is formed so as to only allow insertion of certain canisters, depending on the medicament contained therein.

Preferably, the outlet assembly is formed as a single integral moulding.

According to one embodiment, the outlet assembly is formed such that it comprises all parts of the actuator that comes into contact with the medicament during normal use. Preferably, the main body is provided with an outlet opening for receiving the outlet assembly in a position wherein the mouthpiece extends outside the outlet opening and the nozzle block is arranged in position for receiving the valve stem of the canister.

In such an actuator, only the mouth piece section of the outlet assembly extends outside the main body, thereby minimising its exposed external surface, while still comprising all the parts of the actuator that comes in contact with the medicament. Moreover, the outlet assembly according to this embodiment will be comprised of a very small volume of material.

Preferably, the outlet opening is a lateral opening at one end of the tubular member and arranged to receive the outlet assembly at an angle transverse to the length of the tubular member.

Preferably, the main body and the outlet assembly are configured so as to snap-fit together in that they are provided with complementary snap catch members. According to one embodiment, the snap catch members of both the main body and the outlet assembly are arranged inside the actuator in the assembled state.

Preferably, at least a part of the outlet assembly is configured so as to deform and optionally break on withdrawal of the outlet assembly from the main body so as to prevent re-use of the inhaler.

Preferably, the nozzle block is connected and supported by the mouthpiece providing an essentially free flow of air about the nozzle block.

Preferably, the nozzle block is attached to the mouthpiece by a connection having at least one member connecting a lower part of the mouthpiece with a lower part of the nozzle block and at least one member connecting an upper part of the mouthpiece with an upper part of the nozzle block, leaving there between an open path for flow of air during inhalation.

The snap catch members provides for reliable high speed assembly, whereby the two parts of the actuator are assembled in one single step, while the actuator still being robust and reliable. Moreover, when the snap catch arrangement is arranged inside the actuator, it does not contribute to the external appearance of the actuator, at the same time as it makes tampering more difficult.

Preferably, the actuator comprises, one or both of a breath actuation mechanism and a compliance monitor, in particular a dose counter. According to one embodiment the main body comprises one or both of the breath actuation mechanism and the compliance monitor, preferably, the foot comprises one or both of the breath actuation mechanism and the compliance monitor.

According to one embodiment, the outlet assembly is provided in two or more configurations. The two or more outlet assembly configurations may e.g. differ by the orifice size in the nozzle block. In order to achieve full flexibility, the different outlet assembly configurations each can be used with the whole range of main bodies. However, in some situations the outlet assembly of one specific configuration can be limited to be used with a specific range of actuator housings. To be able to identify the outlet assembly configurations, they can differ in physical appearance.

Alternatively or in addition, the different outlet assembly configurations are identified by the physical appearance of a protection cap to be placed over the mouthpiece of the outlet assembly.

The present invention also extends to an inhaler comprising the above-described actuator and a canister containing medicament, a main body and an outlet assembly Preferably, the inhaler is a pressurised metered dose inhaler.

According to one embodiment, the physical appearance of the main body is indicative of the medicament contained in the canister and optionally the dose delivered. Alternatively or in addition thereto the physical appearance of the main body is selected by the patient, from the range of main bodies in order to provide a personalized inhaler.

BRIEF DESCRIPTION OF THE DRAWINGS

A preferred embodiment of the present invention will now be described herein below by way of example only with reference to the accompanying drawings, in which:

FIG. 1 illustrates a perspective view of an inhaler in accordance with a preferred embodiment of the present invention;

FIG. 2 illustrates a side view of the inhaler of FIG. 1;

FIG. 3 illustrates a front view of the inhaler of FIG. 1;

DETAILED DESCRIPTION OF PREFERRED EMBODIMENTS

Figure 4:
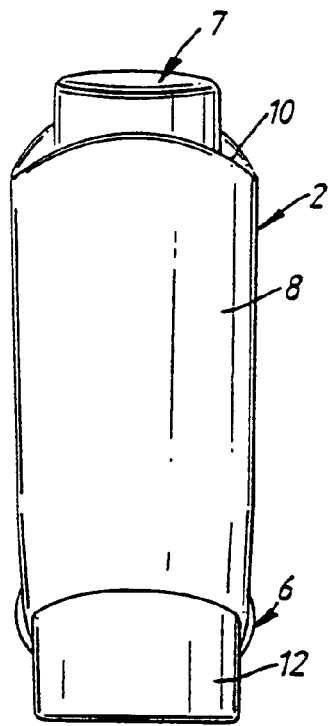
FIG. 4 illustrates a rear view of the inhaler of FIG. 1.
Figure 5:
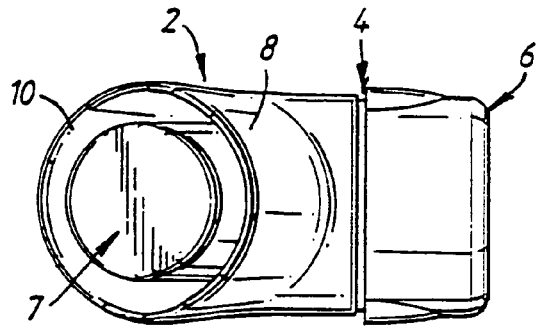
FIG. 5 illustrates a plan view of the inhaler of FIG. 1.
Figure 6:
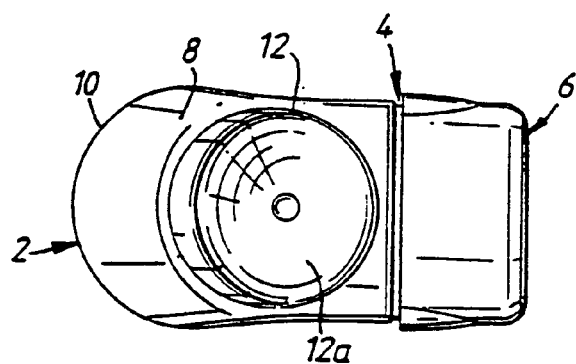
FIG. 6 illustrates an underneath plan view of the inhaler of FIG. 1.
Figure 7:
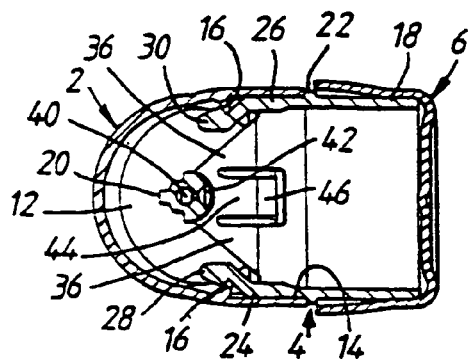
FIG. 7 illustrates a horizontal sectional view (along section A-A) of the inhaler of FIG. 1.
Figure 8:
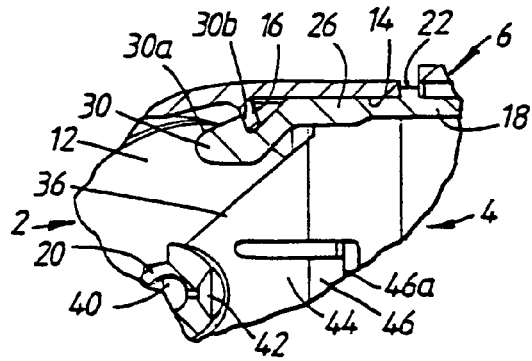
FIG. 8 illustrates in enlarged scale a fragmentary view of the section illustrated in FIG. 7.
Figure 9:
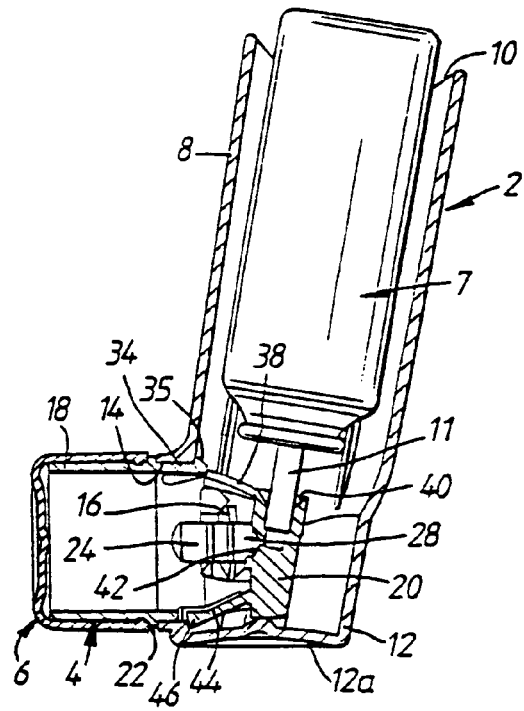
FIG. 9 illustrates a vertical sectional view (along section B-B) of the inhaler of FIG. 1.
Figure 10:
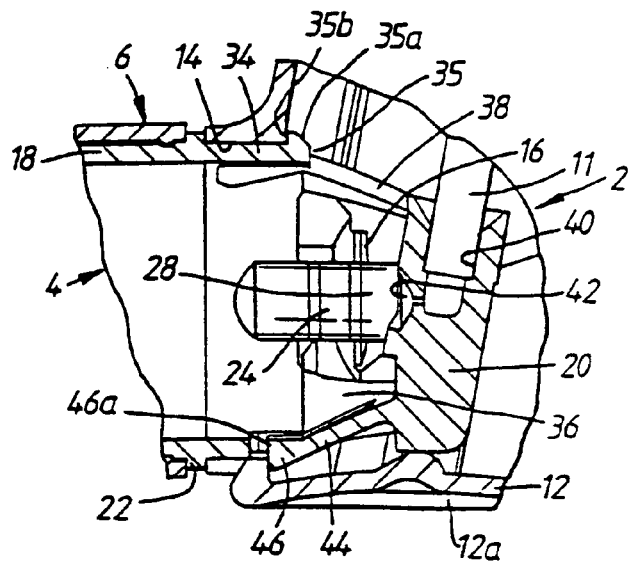
FIG. 10 illustrates in enlarged scale a fragmentary view of the section illustrated in FIG. 9.
Figure 11:
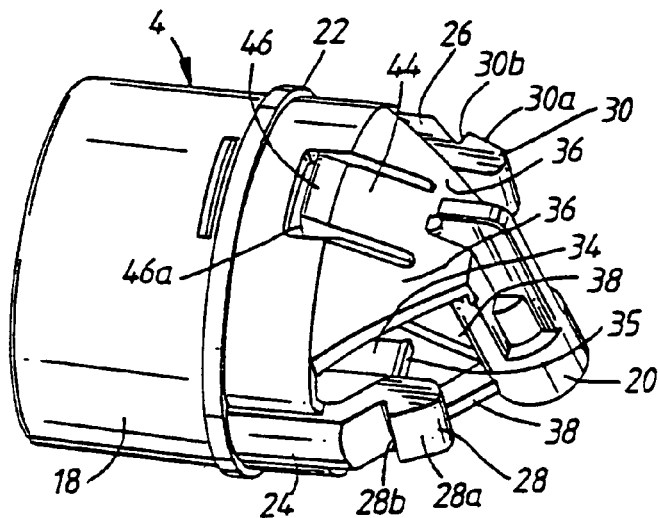
FIG. 11 illustrates a perspective view of the outlet assembly of the actuator of the inhaler of FIG. 1.
Figure 12:
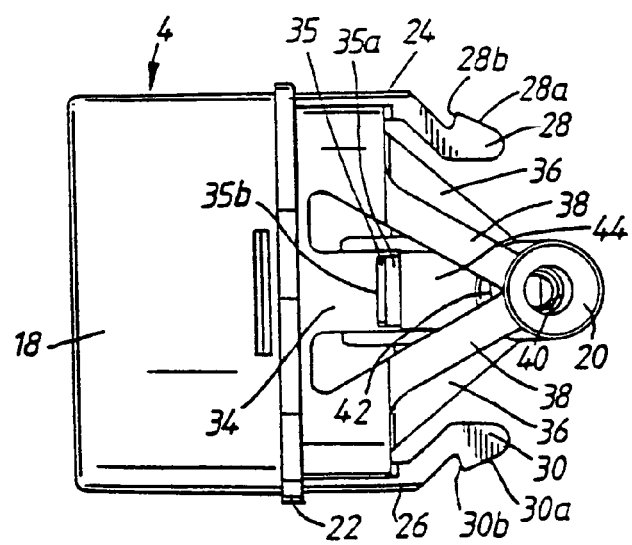
FIG. 12 illustrates a plan view of the outlet assembly of FIG. 11.
Figure 13:
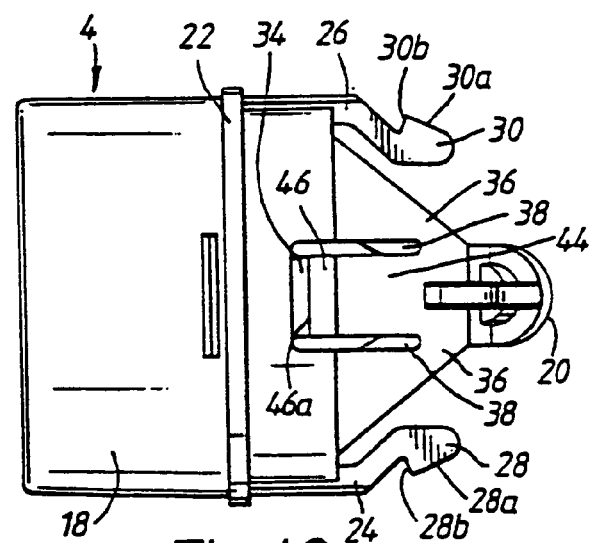
FIG. 13 illustrates an underneath plan view of the outlet assembly of FIG. 11.
Figure 14:
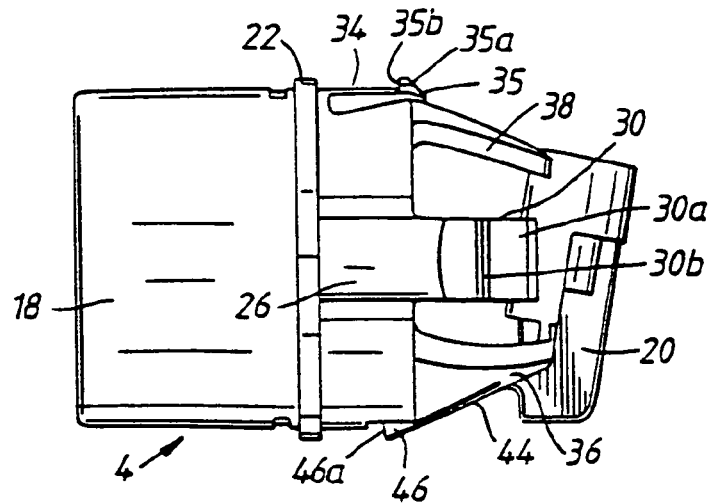
FIG. 14 illustrates a side view of the outlet assembly of FIG. 11.
Figure 15:
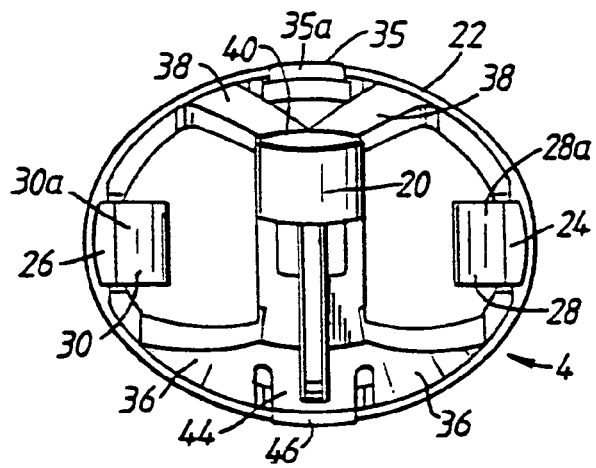
FIG. 15 illustrates a rear view of the outlet assembly of FIG. 11.
Figure 16:
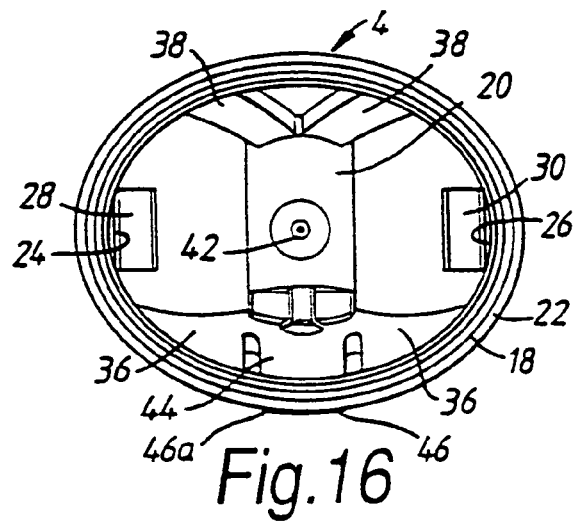
FIG. 16 illustrates a front view of the outlet assembly of FIG. 11.

The inhaler comprises an actuator, which comprises a main body 2, an outlet assembly 4 fitted to a lower part of the main body 2 and a cap 6, and an aerosol canister 7 containing medicament fitted therein.

The main body 2 comprises a tubular member 8 having an opening 10 at one, the upper end thereof into which a canister 7 having a valve stem 11 extending therefrom is in use fitted, and a foot 12 having a bottom surface which includes a recess 12a, in this embodiment concave in shape, for receiving typically a thumb of a user. In an alternative embodiment the foot 12 can be formed with a substantially flat bottom surface. The foot 12 serves to allow the actuator to stand unsupported on a flat surface such that, when the actuator is not in use, it can be stored in an upright position. This is particularly advantageous when a canister 7 is fitted therein, since such canisters 7 should, ideally, be stored with the valve stem 11 directed downwards. The other, lower, end of the tubular member 8 is closed and includes a lateral opening 14, in this embodiment ovoid in shape, into which the outlet assembly 4 is fitted.

The main body 2 further comprises a pair of opposing projections 16 which extend inwardly from the inner surface of the tubular member 8 adjacent the lateral opening 14. The projections 16 are disposed to the sides of the lateral opening 14 and are spaced rearwardly therefrom.

The outlet assembly 4 comprises a tubular section 18, a major part of which defines the mouthpiece which is in use gripped by the lips of a user, and a nozzle block 20 connected thereto.

The tubular section 18 includes a radial outwardly-directed peripheral flange 22. When the outlet assembly 4 is inserted fully into the main body 2, the flange 22 abuts the lateral opening 14 such that the major part of the tubular section 18 extends outwardly of the main body 2.

The outlet assembly 4 further comprises first and second arms 24, 26 which extend rearwardly form respective sides of the tubular section 18. Each of the first and second arms 24, 26 includes a catch member 28, 30 which is adapted to engage with a respective one of the projections 16 on the inner surface of the tubular member 8 when the outlet assembly 4 is inserted fully into the main body 2. The catch members 28, 30 on the first and second arms 24, 26 each include a first surface 28a, 30a which has a rearwardly directed component and acts as a guiding surface, and a second surface 28b, 30b which is substantially orthogonally directed to the longitudinal axis of the outlet assembly 4 and acts as a locking surface.

The outlet assembly 4 further comprises a third arm 34 which extends rearwardly from the top of the tubular section 18. The third arm 34 includes a catch member 35 in the form of an outwardly-directed projection, which, when the outlet assembly 4 is inserted fully into the main body 2, engages behind a part of the tubular member 8 defining the lateral opening 14. The catch member 35 on the third arm 34, as with the catch members 28, 30 on the first and second arms 24, 26, includes a first surface 35a which has a rearwardly directed component and acts as a guiding surface, and a second surface 35b which is substantially orthogonally directed to the longitudinal axis of the outlet assembly 4 and acts as a locking surface.

The nozzle block 20 is connected to the tubular section 18 by first and second pairs of connecting elements 36, 38. The first pair of connecting elements 36 extend between a lower part of the nozzle block 20 and a lower part of the tubular section 18. As will be described herein below, in this embodiment the lower connecting elements 36 are configured to break or be permanently deformed on withdrawal of the outlet assembly 4 from the main body 2. The second pair of connecting elements 38 extend between an upper part of the nozzle block 20 and an upper part of the tubular section 18. The nozzle block 20 includes a tubular bore 40 which extends along the longitudinal axis of the tubular member 8 when the outlet assembly 4 is inserted fully into the main body 2. The tubular bore 40 is open at one, the upper, end and includes a laterally-directed spray orifice 42 at the other, lower, end. The spray orifice 42 is configured to direct a spray into the tubular section 18. In this embodiment the tubular bore 40 is adapted to receive the valve stem 11 of a canister 7.

The outlet assembly 4 further comprises a fourth arm 44 which extends forwardly and downwardly from the nozzle block 20. The distal end of the fourth arm 44 includes a catch member 46 which, when the outlet assembly 4 is inserted fully into the main body 2, engages behind a part of the tubular member 8 defining the lateral opening 14. The catch member 46 on the fourth arm 44 includes a surface 46a which is substantially orthogonally directed to the longitudinal axis of the outlet assembly 4 and acts as a locking surface.

In manufacture, an outlet assembly 4 and a main body 2 are selected according to the requirements, based on colour, shape, etc., for the actuator. The outlet assembly 4 is then inserted into the lateral opening 14 in the main body 2 until the catch members 28, 30 on the first and second arms 24, 26 of the outlet assembly 4 engage with the respective projections 16 on the inner side surface of the tubular member 8 of the main body 2, and the catch members 34, 46 on the third and fourth arms 34, 44 of the outlet assembly 4 engage behind respective parts of the tubular member 8 defining the lateral opening 14. A canister 7 is then passed into the tubular member 8 of the main body 2 through the upper opening 10 such that the valve stem 11 of the canister 7 is located in the tubular bore 40 in the nozzle block 20. The inhaler is then ready for use.

By the provision of catch members the outlet assembly 4 is held in the main body 2 and the outlet assembly 4 cannot be non-destructably detached from the main body 2. As mentioned herein above, the outlet assembly 4 is configured to break or be permanently deformed if withdrawn from the main body 2 and thereby render the outlet assembly 4 and hence the actuator unusable. In this embodiment this is achieved by configuring the lower connecting elements 36 connecting the tubular section 18 and the nozzle block 20 of the outlet assembly 4 to break or be permanently deformed on withdrawal of the outlet assembly 4 from the main body 2.

Finally, it will be understood by a person skilled in the art that the present invention is not limited to the described embodiment but can be modified in many different ways within the scope of the appended claims.

The invention claimed is:

1. An actuator for an inhaler for delivering medicament by inhalation, comprising:
   a main body comprising a tubular member for receiving a canister containing medicament and having a valve stem extending therefrom; and
   an outlet assembly, as a part formed separately of the main body, comprising a mouthpiece for guiding medicament to the mouth of a user and a nozzle block for receiving the valve stem of the canister and delivering medicament from the canister into the mouthpiece; wherein:
   the actuator belongs to a range of inhaler actuators,
   the outlet assembly is a common part for the range of actuators,
   members of the range of actuators differ by a physical appearance of the main body, the outlet assembly is formed such that it comprises all parts of the actuator that come into contact with the medicament during normal use, the main body and the outlet assembly are provided with complementary snap catch members so as to snap-fit together, and the tubular member is provided with a lateral opening at one end of the tubular member for receiving the outlet assembly at an angle transverse to the length the tubular member.

2. The actuator according to claim 1, wherein the members of the range of actuators differ in that their respective main bodies are made of materials having different constitution.

3. The actuator according to claim 1, wherein the members of the range of actuators differ by the colour of their respective main bodies.

4. The actuator according to claim 1, wherein the members of the range of actuators differ by the surface finish of their respective main bodies.

5. The actuator according to claim 1, wherein the members of the range of actuators differ by the decoration of their respective main bodies.

6. The actuator according to claim 1, wherein the members of the range of actuators differ by the shape of their respective main bodies.

7. The actuator according to claim 6, wherein the main body is given a particular shape that appeals to a specific patient group.

8. The actuator according to claim 6, wherein the main body is shaped to resemble an object other than an actuator for an inhaler.

9. The actuator according to claim 8, wherein the main body is shaped to resemble an animal, a cartoon figure, a plant, a fruit, a toy, a car, or an electronic device.

10. The actuator according to claim 6, comprising a protection cap to be placed over the mouthpiece of the outlet assembly, said cap being an integrated part of the particular shape in the protecting position.

11. The actuator according to claim 1, wherein the main body comprises attachment means for a key strap, a belt strap or a wrist strap to enable it to be carried around the neck or the wrist of the patient.

12. The actuator according to claim 1, wherein the main body is formed so as to only allow insertion of certain canisters, depending on the medicament contained therein.

13. The actuator according to claim 1, wherein the outlet assembly is formed as a single integral moulding.

14. The actuator according to claim 1, wherein the main body is provided with an outlet opening for receiving the outlet assembly in a position wherein the mouthpiece extends outside the outlet opening and the nozzle block is arranged in position for receiving the valve stem of the canister.

15. The actuator according to claim 1, wherein the snap catch members of both the main body and the outlet assembly are arranged inside the actuator in the assembled state.

16. The actuator according to claim 1, wherein at least a part of the outlet assembly is configured so as to deform and optionally break on withdrawal of the outlet assembly from the main body so as to prevent re-use of the inhaler.

17. The actuator according to claim 1, wherein the nozzle block is connected and supported by the mouthpiece providing an essentially free flow of air about the nozzle block.

18. The actuator according to claim 17, wherein the nozzle block is attached to the mouthpiece by a connection having at least one member connecting a lower part of the mouthpiece with a lower part of the nozzle block and at least one member connecting an upper part of the mouthpiece with an upper part of the nozzle block, leaving there between an open path for flow of air during inhalation.

19. The actuator according to claim 1, further comprising one or both of a breath actuation mechanism and a compliance monitor.

20. The actuator according to claim 19, wherein the main body comprises one or both of the breath actuation mechanism and the compliance monitor.

21. The actuator according to claim 19, further comprising a dose counter.

22. The actuator according to claim 1, wherein two or more outlet assemblies are provided each with different configurations.

23. The actuator according to claim 22, wherein the outlet assembly configuration differs by the size of an orifice in the nozzle block.

24. The actuator according to claim 22, wherein the different outlet assembly configurations each can be used with the whole range of main bodies.

25. The actuator according to claim 22, wherein the outlet assembly of one specific configuration is limited to be used with a specific range of actuator housings.

26. The actuator according to claim 22, wherein the different outlet assembly configurations differ in physical appearance.

27. The actuator according to claim 22, comprising a protection cap to be placed over the mouthpiece of the outlet assembly wherein the different outlet assembly configurations are identified by the physical appearance of the protection cap.

28. An inhaler comprising the actuator according to claim 1 and a canister containing medicament.

29. The inhaler according to claim 28, wherein the inhaler is a pressurised metered dose inhaler.

30. The inhaler according to claim 28, wherein the physical appearance of the main body is indicative of the medicament contained in the canister and optionally the dose delivered.

31. The inhaler according to claim 28, wherein the physical appearance of the main body is selected by the patient, from the range of main bodies in order to provide a personalized inhaler.

32. An outlet assembly of an actuator for an inhaler for delivering medicament by inhalation, the outlet assembly being a part formed separately of a main body of the actuator, the outlet assembly comprising a mouthpiece for guiding medicament to the mouth of a user and a nozzle block for receiving the valve stem of the canister and delivering medicament from the canister into the mouthpiece, the main body of the actuator comprising a tubular member for receiving a canister containing medicament and having a valve stem extending therefrom wherein:

the outlet assembly is arranged to be received in a lateral outlet opening at one end of the tubular member at an angle transverse to the length thereof, the outlet assembly is formed such that it comprises all parts of the actuator that come into contact with the medicament during normal use, the main body is provided with an outlet opening and the outlet assembly is arranged to be received in a position wherein the mouthpiece extends outside the outlet opening and the nozzle block is inserted through the outlet opening and arranged in position for receiving the valve stem of the canister, and the outlet opening is a lateral opening at one end of the tubular member and the outlet assembly arranged to be inserted into the outlet opening at an angle transverse to the length of the tubular member.

33. The outlet assembly according to claim 32, wherein it is formed as a single integral moulding.

34. The outlet assembly according to claim 32, wherein it is provided with snap catch members that are complementary to snap catch members of the main body.

35. The outlet assembly according to claim 32, wherein at least a part of the outlet assembly is configured so as to deform and optionally break on withdrawal of the outlet assembly from the main body so as to prevent re-use of the inhaler.

36. The outlet assembly according to claim 32, wherein the nozzle block is connected and supported by the mouthpiece providing an essentially free flow of air about the nozzle block.

37. The outlet assembly according to claim 36, wherein the nozzle block is attached to the mouthpiece by a connection having at least one member connecting a lower part of the mouthpiece with a lower part of the nozzle block and at least one member connecting an upper part of the mouthpiece with an upper part of the nozzle block, leaving there between an open path for flow of air during inhalation.

* * * * *